United States Patent [19]

Van der Salm

[11] Patent Number: Plant 7,272

[45] Date of Patent: Jul. 17, 1990

[54] LILIUM "ROYAL DUTCH"

[76] Inventor: Gerardus C. Van der Salm, Rte. 4, Box 422, Woodland, Wash. 98674

[21] Appl. No.: 350,019

[22] Filed: May 9, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Klarquist, Sparkman, Campbell, Leigh & Whinston

[57] ABSTRACT

A new variety of hybrid lily plant bearing large clusters of flowers of excellent form and long persistence, both on the plant and as cut flowers. The flowers of the new plant are particularly characterized by their unusually large, thick-textured melon orange flowers with lightly undulating tepal margins. This combination is completely new in the upright Asiatic divisions of lilies suited to forcing and to mass commercial cultivation. The plant is highly resistant to disease and shows high tolerance of virus. It is an excellent garden plant. The bulbs may be precooled and forced for cut-flower production. The new variety is vigorous and is a good grower and propagator.

1 Drawing Sheet

BACKGROUND OF THE INVENTION

My new variety of hybrid lily plant originated as a seedling selected from a group of seedlings at Julianadorp, the Netherlands. The seedlings were planted as a result of breeding efforts carried on by me since 1976; the final cross that produced my new variety, which I call "Royal Dutch", was made in 1982. The breeding efforts had as their objective the production of orange upright Asiatic lilies with extremely large, thick-textured flowers, well suited to forcing for cut-flower production out of season, heretofore unknown in the lily breeding art.

I achieved the desired objective by extensive interpollinations among many hybrid lily cultivars.

The flowers of my new lily are characterized by an upright orientation, their warm melon-orange color, and in particular by their unusually large size and thick texture. In addition, my new variety possesses to a high degree desirably characteristics of hybrid vigor, great hardiness, and disease resistance. My new variety possesses the desired characteristics of excellence of form, color, and habit. The flowers of my new variety are produced on a single stalk. My Royal Dutch variety is vigorous and a good grower and propagator, as observed at Julianadorp, the Netherlands, and at Woodland, Wash.

My new variety is well suited to forcing out of season when the bulbs are dug at the appropriate time and properly precooled.

My new variety of lily plant has been asexually reproduced by me and under my direction at Julianadorp, the Netherlands and at Woodland, Wash. Successive generations produced by bulb scale propagation and by natural propagation from bulblets have demonstrated that the novel and distinctive characterstics of my new variety are fixed and hole true under asexual propagation from generation to generation.

BRIEF DESCRIPTION OF THE DRAWING

My new variety of lily plant is illustrated in the accompanying photographic drawing, which shows the open bloom in full color and illustrates the flower form, the tepal arrangement, the connection of the flower to the stem, and in particular the novel and distinctive large flower size and tepal thickness and lightly undulating tepal margins.

DETAILED DESCRIPTION

The following is a detailed description of my new variety of Asiatic hybrid lily, with nomenclature according to the International Lily Register (Royal Horticultural Society of London, England, Second Edition, 1969), and with color designations according to the Color Chart of The Royal Horticultural Society, published by the Society in 1966.

The Plant

Origin: Seedling.

Seed parent: Unnamed seedling.

Pollen parent: Unnamed seedling.

Commercial classification: Hybrid Lilium clone.

Horticultural classification: Division I-A, upright Asiatic hybrid lily, according to the Horticultural Classification of lilies, Royal Horticultural Society of London.

Form: Single stem, erect and stately.

Height: 80 to 100 cm from bulbs 15 to 18 cm in circumference, provided their light levels are adequate; low light levels may cause "stretching."

Growth: Vigorous and upright.

Foliage quantity: Abundant.

Size of leaf: Averages 8 to 12 cm long × 8 to 12 mm wide.

Shape of leaf: Lanceolate (pointed).

Texture: Leathery and glossy.

Color: Medium green, lighter on lower side, with no anthocyanin pigmentation.

Bulb size: Any size, ranging to 25 cm circumference commercially.

Bulb color: White.

The Bud

Form: Obtuse, ovoid, and long.

Size: 9 to 10 cm long and 8 cm in circumference just prior to opening.

Opening: Bud opens slowly, in response to morning light; this takes about one hour.

Color; RHS CC greyed orange 160 C, just prior to opening. Bud color deepens gradually from green to orange as the buds mature, and midribs may still show a green cast at maturity.

Penduncle: Averages 4 to 6 cm, but it may elongate if light levels are too low or if bulbs have been improperly stored prior to forcing. Color is medium green with no anthocyanin overlay.

The Flower

Blooming habit: Annually in mid season; flowers once and profusely.

Size: Flowers are very large-sized for Asiatic hybrids; they average 18 to 21 cm in diameter. The tepals are unusually broad as well; the outer tepals average 3 cm wide, and the inner tepals average 3.5 to 5 cm wide. The unusual thickness of the tepals causes the margins to undulate slightly as the tips recurve.

Borne: In a single racemic inflorescence producing 8 to 9 buds (from a bulb 18 cm in circumference).

Shape: First open in cup shape, which flattens as tepals recurve somewhat by their second day.

Tepalage: Typical of genus Lilium, with 6 imbricated tepals.

Tepal color: Flowers are distinguished by their warm melon orange coloring, RHS CC orange 24 B, shading to RHS CC orange 28 B-C at the base of the tepals. Color is deepest just above the nectaries and along the tepal midrib. The color may be slightly deeper under conditions of intense light; it may be slightly lighter if light levels are too low.

Tepal spotting: Small spots of deep maroon (RHS CC 187 A) cover the basal third of each tepal.

Tepal longevity: Tepals stay on stems about three weeks.

Pedicel length: Average 6 to 12 cm long.

Pedicel color: Medium green with no plum overlay.

Pedicel form: Sturdy and ascending up to 45 degrees from the horizontal. Bears secondary buds.

Color changes: Color is slightly deeper when light levels are intense and slightly lighter when light levels are low.

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting, both on the plant and as a cut-flower.

The Reproductive Organs

Stamens and anthers: Arrangement typical of genus Lilium. Six stamens with soft orange (RHS CC orange 24 D) filaments 5 cm long.

Pollen and anthers (dehisced): Pollen is RHS CC greyed orange 171 A.

Pistil: One in number, 5 cm long.

Stigma: Soft orange overlaid with very light plum, medium in size.

Characteristics of ovary: Characteristic of genus Lilium.

The Fruit

Fertility: The fruit is sterile.

Shape: Ovoid.

Color at maturity: Soft brown.

My new variety of Asiatic hybrid lily most nearly resembles "Melon Time," but my new variety has much larger flowers of thicker texture, with lightly undulating tepal margins. My new variety also has copious spotting on the basal third of each tepal.

I claim:

1. A new and distinctive variety of Asiatic hybrid lily plant substantially as herein shown and described, characterized by its large size and thickness of its melon orange flowers with their slightly undulating tepal margins and spotting on basal third of each tepal.

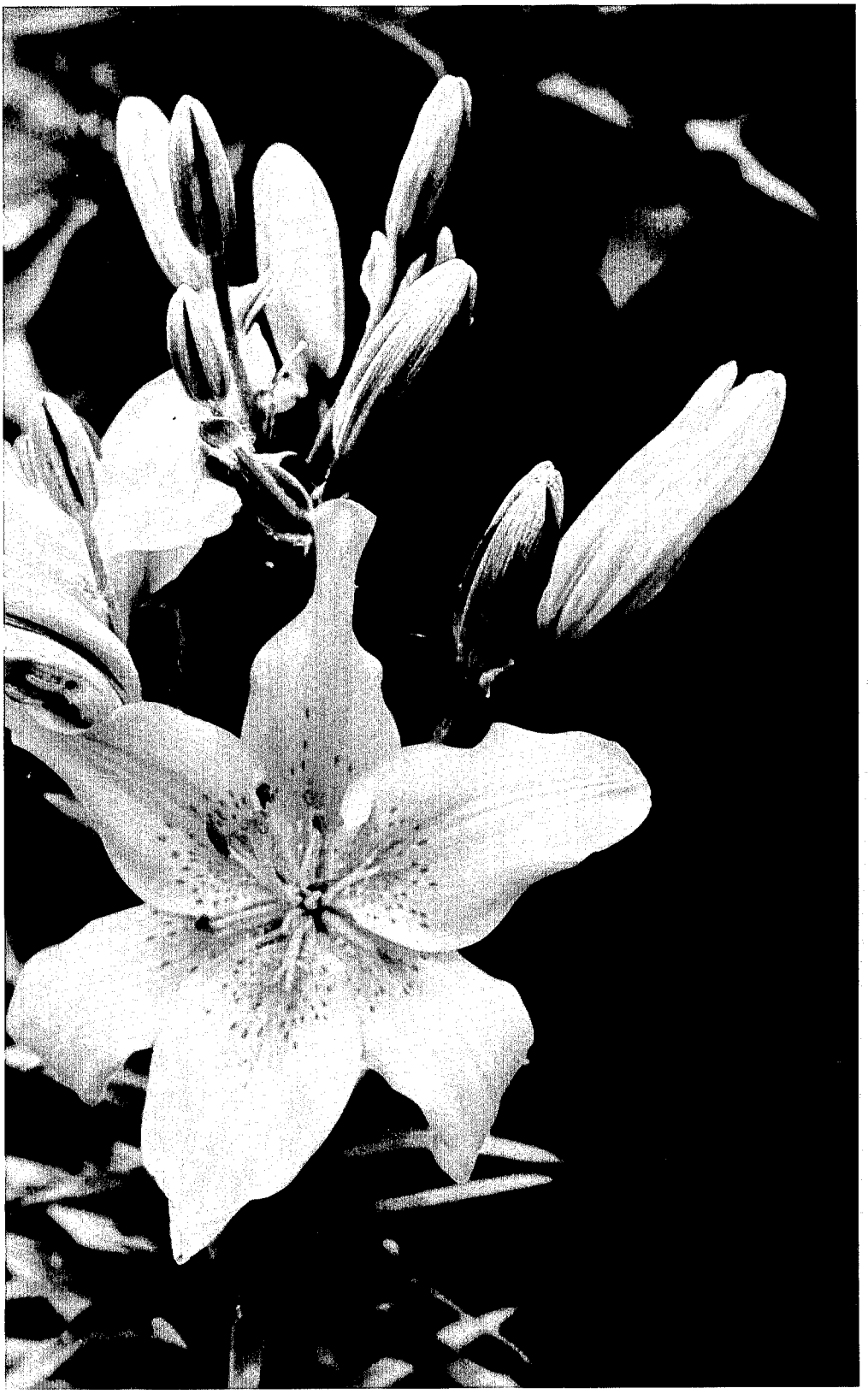

* * * * *